United States Patent [19]

Belykh et al.

[11] Patent Number: 4,492,226
[45] Date of Patent: Jan. 8, 1985

[54] DEVICE FOR UNITING BONE FRAGMENTS

[75] Inventors: Sergei I. Belykh, Moscow; Anatoly D. Moschensky, Malakhovka; Anatoly B. Davydov, Moscow; Gely G. Pershin, Moscow; Boris A. Smirnov, Moscow; Mikhail V. Gromov, Moscow, all of U.S.S.R.

[73] Assignee: Vsesojuzny Nauchno-Issledovatelsky I Ispytatelny Institut Meditsinskoi Tekhniki, Moscow, U.S.S.R.

[21] Appl. No.: 83,310

[22] Filed: Oct. 10, 1979

[51] Int. Cl.³ .............................................. A61F 5/04
[52] U.S. Cl. ................................................ 128/92 BC
[58] Field of Search ........... 128/92 BC, 92 BA, 92 D, 128/92 G

[56] References Cited

U.S. PATENT DOCUMENTS 3,760,802  9/1973  Fischer et al. ................. 128/92 BC
3,986,504  10/1976  Avila ............................... 128/92 BC
4,016,874  4/1977  Maffei et al. .................... 128/92 BC

FOREIGN PATENT DOCUMENTS 419003  3/1974  U.S.S.R. ............................... 128/92

OTHER PUBLICATIONS

"Intraosteal Fixation with Metal Rod for Treating Fractures of Long Tubular Bones" by Dubrov, Medgiz Publ. House, Moscow, 1961, pp. 52-61.
"Threaded Fixing Member for Intramedullar Compression Osteosynthesis", by V. Lyzhin, Meditsina Publ. House, Moscow-Kharkov, No. 8, 1971, pp. 78-80.

Primary Examiner—John D. Yasko
Assistant Examiner—C. W. Shedd
Attorney, Agent, or Firm—Fleit, Jacobson, Cohn & Price

[57] ABSTRACT

A device for uniting bone fragments comprises a rectilinear body and a contrivance for fixing it in the coapted bone fragments. The contrivance for fixing the body in the coapted bone fragments is formed by thrust members being the portions of the body located at the opposite ends thereof and having holes coaxial with the body; the holes being shaped as frustums of cones facing with their greater bases the ends of the body, and having annular grooves in the wall thereof, and cone-shaped inserts with annular ridges adapted to be introduced into the conical holes for wedging apart the body. The body has longitudinal through slots within the zones of the holes. The length of the device is less than the total length of the coapted bone fragments so as to be located fully within the bone tissues.

5 Claims, 2 Drawing Figures

DEVICE FOR UNITING BONE FRAGMENTS

SCOPE OF CLAIM FOR PATENT

1. A device for uniting bone fragments, comprising a body and a means of fixing said body in the coapted bone fragments, characterized in that the means of fixing the body (1) in the coapted bone fragments is formed by thrust members which are in fact the portions of the body (1) located at the opposite ends thereof and having holes (2) coaxial with the body (1), said holes being shaped as frustums of cones facing with their greater bases the ends of the body, whereas the bore surfaces of said holes have annular grooves (3), and cone-shaped inserts (4, 5) having annular ridges (7, 8) and adapted to be introduced into the holes (2) so as to wedge apart the body which is provided with longitudinal through slots (6) located within the zones of the holes (2); the device being claimed features its length less than a total length of the coapted bone fragments so as to be arranged fully in the bone tissues.

2. A device for uniting bone fragments according to claim 1, characterized in that longitudinal recesses (11) are provided on the outside surface of the body (1).

DETAILED DESCRIPTION OF THE INVENTION

The present invention relates to medical equipment and has particular reference to devices for uniting bone fragments.

The present invention can find preferable application for fixing the coapted bone fragments, such as those of the shin, arm, forearm, etc.

Known in the present state of the medical art are devices for uniting bone fragments shaped as rods or pins made of diverse materials and adapted to be driven into the medullary canal by hammering (cf. "Intraosseous fixation with a metal rod in fractures of long tubular bones" by Ya. G. Dubrov, Meditsina Publishers, Moscow 1961), screwing in (cf. "Orthopedics, traumatology and prosthetics" No. 8, 1971), or by fixing one of the rod ends in the medullar canal with the help of thrust members (cf. USSR Inventor's Certificate No. 419,003).

The known device of the character set forth hereinbefore by Fisher and Muller protected by USSR Inventor's Certificate No. 419,003 comprises a sleeve-like body carrying at one end a thrust member and at the other end, a screw. The thrust member consists of shoulders and a thrust head, whereas the screw is adapted for retracting the thrust head and wedging the shoulder apart in the medullar canal.

When operating the known device is introduced for its entire length into a preliminarily bored out medullary canal, whereupon the screw projecting beyond the bone tissue is rotated so as to retract the thrust head in the shoulders, thus wedging apart the thrust member.

The aforesaid known device provides for fixation of bone fragments for a period of their consolidation. However, the fixation process carried out by said device results in traumas inflicted upon the surrounding tissues and the bone end both at the moment of fixation and within the consolidation process. Moreover, an adequately wide range of the sleeve-like bodies must be at surgeon's disposition before the operation, both with respect to the diameter and length so as to suit the size of bones to be operated and location of a fracture lengthwise the bone.

In addition, small contact area of the thrust member with the medullary canal needs the provision of a reasonably high local pressure upon the walls of the medullary canal, which results in necrosis and weakened fixation of the sleeve-like body within the period of consolidation. Once the consolidation of bone fragments has occurred a repeated surgical intervention is involved for removal of the device for uniting bone fragments from the bone operated upon.

It is an object of the present invention to provide a device for uniting bone fragments which would ensure a reliable fixation of bone fragments for an entire period of their consolidation.

It is another object of the present invention to provide a device for uniting bone fragments which would preclude any injury to the external bone surface and the surrounding soft tissues and would not impede regeneration of bone marrow just after fixation of bone fragments.

It is one more object of the present invention to provide such a device for uniting bone fragments that would not involve its matching as for length and would dispense with any repeated operation for extracting said device after consolidation of bone fragments.

The essence of the present invention resides in that in a device for uniting bone fragments, comprising a rectilinear body and a means of its fixing in the coapted bone fragments, according to the invention said means of fixing the body in the coapted bone fragments is made up by thrust members which are in fact the portions of the body located at the opposite ends thereof and having holes coaxial with the body and shaped as frustums of cones with their greater bases facing the ends of said body, whereas the bore surfaces of said holes have annular grooves, and cone-shaped inserts having annular ridges and adapted to be introduced into the holes so as to wedge apart the body which is provided with logitudinal through slots located within the zones of said holes; the device in question having its length less than a total length of the coapted bone fragments so as to be arranged fully in the bone tissues.

Such a constructional arrangement of the device for uniting bone fragments provides for a reliable fixation of bone fragments throughout the period of their consolidation, precludes injury to the bone surface and the surrounding soft tissues as having no parts protruding beyond the bones being handled, puts no obstacles to regeneration of bone marrow within a greater portion of the medullary canal as the length of the device is substantially less than that of the above canal, involves neither matching of the device as for length in order to suit the localization of the fractured bone nor performing any repeated operation.

It is expedient that longitudinal recesses be provided on the outside body surface which will favour regeneration of the bone marrow within the period of consolidation of bone fragments.

BRIEF DESCRIPTION OF THE DRAWINGS

Given below is a detailed description of some illustrative embodiments of the present invention given by way of example with reference to the accompanying drawings, wherein.

DETAILED DESCRIPTION OF A PREFERRED EMBODIMENT

Figure 1:
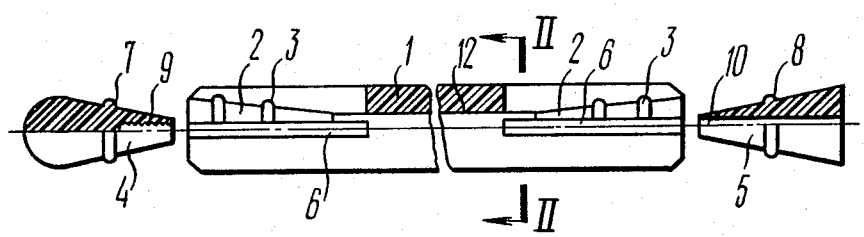
FIG. 1 illustrates a device for uniting bone fragments, according to the invention.
Figure 2:
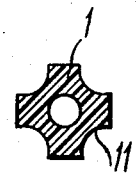
FIG. 2 is a section taken along the line II—II in FIG. 1.

The herein-proposed device for uniting bone fragments comprises a body 1 (FIG. 1) and a means of its fixing in the coapted bone fragments, said means being established by thrust members made as the portions of the body 1 located at the opposite ends thereof and provided with holes 2 coaxial with the body 1 and shaped as frustums of cones facing with their greater bases the ends of the body 1, the bore surfaces of said holes having annular grooves 3, whereas respective inserts 4 and 5 are provided in the means in question. The inserts 4 and 5 are cone-shaped and are adapted to be introduced into the holes 2 so as to wedge apart the body 1 which is provided with longitudinal through slots or recesses 6 located within the zones of the holes 2. The outside surfaces of the inserts 4 and 5 have annular ridges 7 and 8 adapted to mate with the cone-shaped grooves 3. The insert 4 may have a threaded hole 9, while the insert 5, a through hole 10. For better regeneration of the bone marrow, longitudinal recesses 11 (FIG. 2) are provided on the outside surface of the body 1. The overall length of the device proposed herein is less than a total length of the coapted bone fragments so that said device is fully arranged in the bone tissues.

The device for fixing bone fragments operates as follows.

The device for uniting bone fragments is placed in a contrivance (not shown) for its introduction into the bone tissues, e.g., a steel pin threaded at one end, which is passed through the opened hole in the insert 5, an axial 12 (FIG. 1) of the body 1 intercommunicating the holes 2, and it is then screwed into the threaded hole 9 of the insert 4. Next the proposed device carried by said contrivance is introduced through a prepared inlet opening (not shown) into the canal of the coapted bone fragments for such a depth that both ends of the device be spaced nearly equally apart from the line of fracture. Then the inserts 4 and 5 are drawn into the holes 2 shaped as frustums of cones until the annular ridges 7 and 8 match together with one of the annular grooves 3.

Thus, the portions of the body 1 provided with the holes 2 are wedged apart due to the through recesses 6 and thust against the surface of the canal formed by the coapted bone fragments, thereby fixing the latter. Thereupon the contrivance for introducing the herein-proposed device into the bone fragments is extracted.

What is claimed is:
1. A device for uniting bone fragments, comprising:
a rectilinear body having a longitudinally-extending through bore formed therein;
holes coaxial to said body, provided at opposite end portions thereof and shaped as frustums of cones facing with their greater bases the respective ends of said body;
annular grooves made in the bore surfaces of said holes;
longitudinal through slots made in said end portions of said body within the zones of said holes;
cone-shaped inserts adapted for being introduced into said holes so as to wedge apart said body at the both ends thereof;
annular ridges made on said inserts and adapted to fit in said annular grooves so as to hold said inserts in positions wedging apart said end portions of said body;
said device featuring its length less than a total length of the coapted bone framents so that it can be arranged fully in the bone tissues.

2. A device for uniting bone fragments as claimed in claim 1, wherein the outer surface of said body has longitudinal recesses along the full length of the body.

3. A device for uniting bone fragments comprising:
a rectilinear body having holes shaped as frustums of cones coaxial with, and at opposite ends of, said body, with the greater bases of the cones being located at ends of said body;
cone-shaped inserts insertable into said holes; and
means for interlocking said inserts in said holes comprising at least one cooperating annular groove and annular ridge, said annular groove being formed in surfaces of both of said holes intermediate the bases of the frustums and said annular ridge being formed in surfaces of both of said inserts, said annular groove cooperating with said annular ridge to hold one of said inserts in a position wedging apart a respective end portion of said body.

4. A device according to claim 3, wherein the length of said body after insertion of said inserts is less than the total length of joined bone fragments so that said device is located within the joined bone fragments.

5. A device for uniting bone fragments as claimed in claim 3, wherein the outer surface of said body has longitudinal recesses along the full length thereof.

* * * * *